United States Patent [19]

Fisher

[11] Patent Number: 5,002,561
[45] Date of Patent: Mar. 26, 1991

[54] PROTECTIVE HAND FORCEPS

[76] Inventor: Frank E. Fisher, 1630 Borealis, S.E., Rio Rancho, N. Mex. 87124

[21] Appl. No.: 562,456

[22] Filed: Aug. 2, 1990

Related U.S. Application Data

[63] Continuation of Ser. No. 395,293, Aug. 17, 1989, abandoned, which is a continuation of Ser. No. 195,103, May 16, 1988, abandoned.

[51] Int. Cl.$^5$ .............................................. A61B 17/30
[52] U.S. Cl. .................................... 606/210; 606/205; 128/917; 294/99.2
[58] Field of Search ................. 2/21, 160, 161 R, 163; 606/205, 207, 210, 131, 133, 157; 128/917, 918; 81/177.3; 294/99.2, 25; 433/157; 30/111, 112, 232, 291, 298, 123.5

[56] References Cited

U.S. PATENT DOCUMENTS

| | | |
|---|---|---|
| 126,565 | 5/1872 | Mitchell . |
| 137,918 | 4/1873 | Harts .................................. 30/298 X |
| 1,055,838 | 3/1913 | Torrance ............................. 2/161 R |
| 1,362,461 | 12/1920 | Anast ..................................... 2/21 |
| 2,637,031 | 5/1953 | Friedman .................................. 2/21 |
| 3,735,426 | 5/1973 | Horvath .................................. 3/12.8 |

FOREIGN PATENT DOCUMENTS

| | | | |
|---|---|---|---|
| 7032 | 7/1899 | Fed. Rep. of Germany ........ 294/25 |
| 1369291 | 6/1964 | France ..................................... 2/21 |
| 655229 | 1/1963 | Italy ........................................ 2/21 |

Primary Examiner—Michael H. Thaler
Attorney, Agent, or Firm—Robert W. Weig; Deborah A. Peacock; Donovan F. Duggan

[57] ABSTRACT

The disclosure is directed to hand forceps usable by medical personnel, and others, to protect them from incurring injury and contamination when handling intravenous (IV) needles, suture needles, scalpels, and vessels containing body fluids, during surgical procedures and otherwise. The forceps comprises thumb and index finger encasing portions hinged together. A skirt area extends over a portion of the back of a user's hand from the base of the thumb and index finger encasing portions. The forceps can be made of various plastics, metals, and the like and can be coated with a trauma preventing, invasive device snagging layer of latex or similar material. Outwardly extending protective flanges can be provided longitudinally disposed on the thumb and index finger encasing portions. A central shield can also be provided.

22 Claims, 5 Drawing Sheets

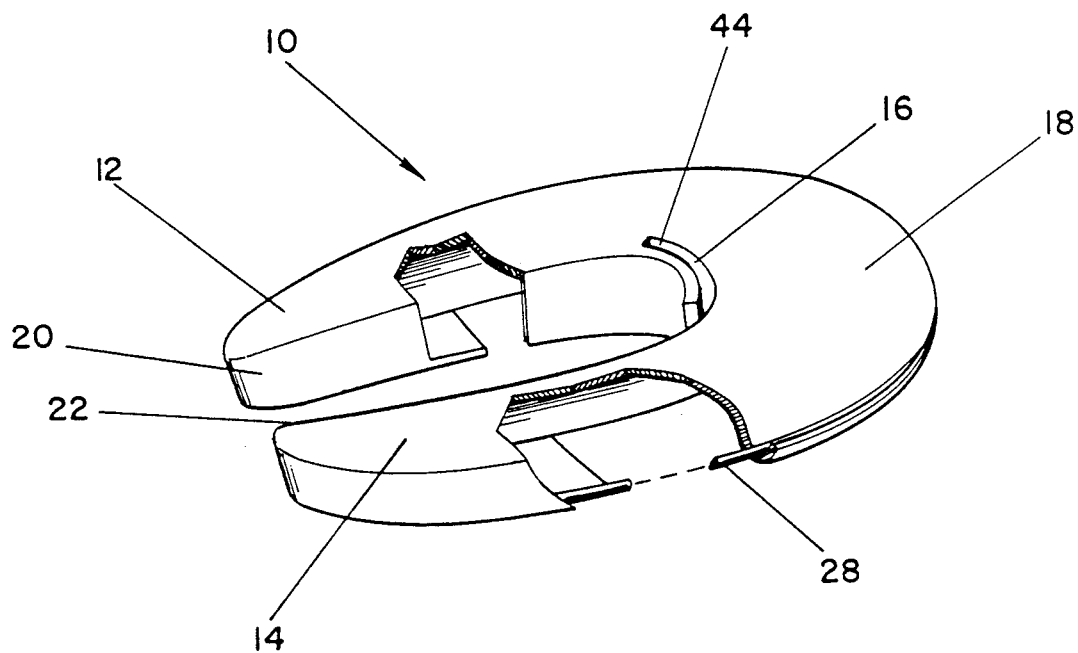
FIG—1
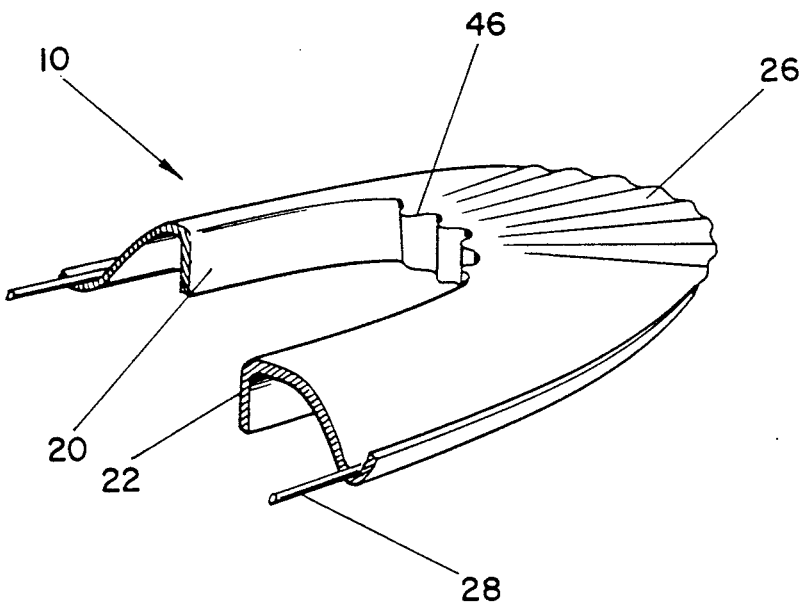
FIG—2

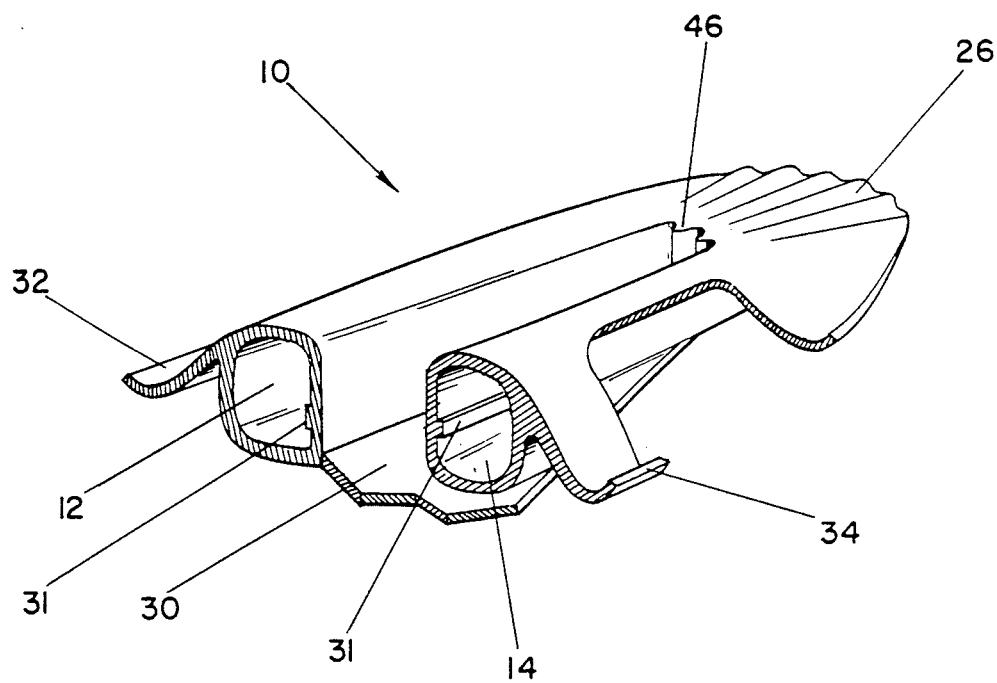
FIG—3
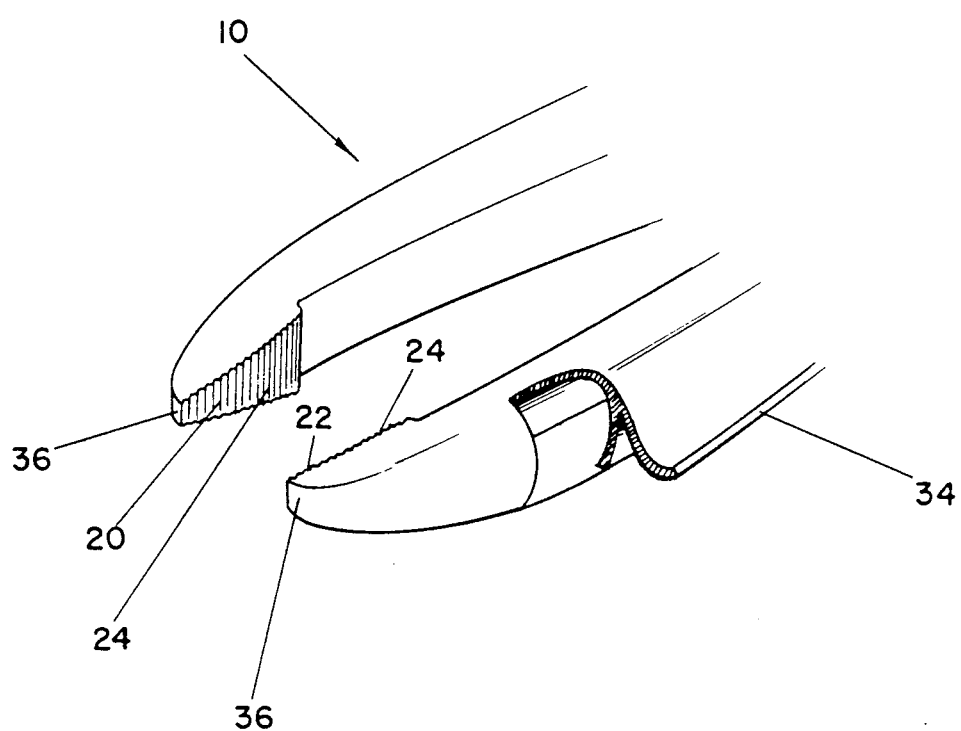
FIG—4

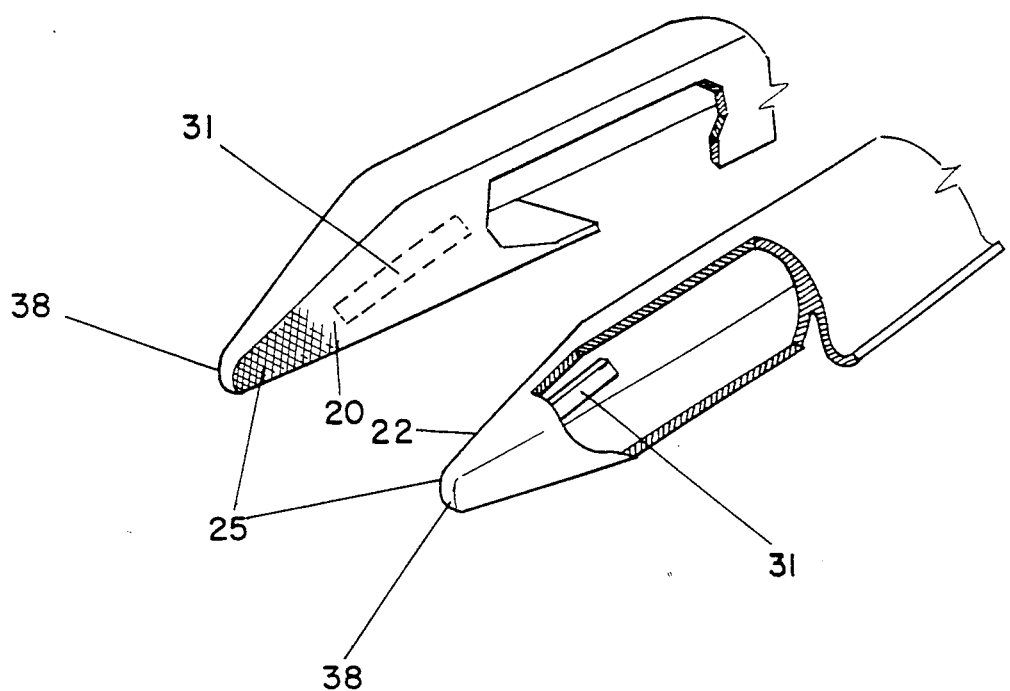
FIG—5
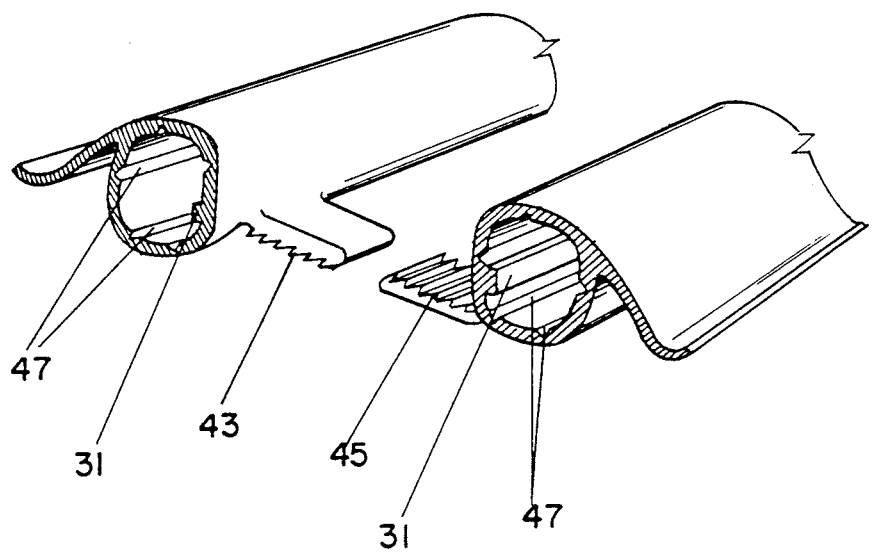
FIG—6

PROTECTIVE HAND FORCEPS

This application is a continuation of application Ser. No. 07/395,293, filed Aug. 17, 1989, entitled Protective Hand Forceps, now abandoned, which is a continuation of application Ser. No. 07/195,103, filed May 16, 1988, now abandoned.

BACKGROUND OF THE INVENTION

With the increase in contagious body fluid carried organisms such as the Acquired Immune Deficiency Syndrome (AIDS) virus, there is an increasing need to protect medical, health and other workers who can come into contact with the body fluids of others. In particular, there is a need to protect personnel providing personal care, such as physicians, nurses and medical workers who administer intravenous needles and surgical procedures, and handle vessels such as glass test tubes. Thus, the need exists to prevent such personnel from sticking themselves with used (and therefore possibly contaminated) needles, cutting themselves with scalpels during surgical procedures and otherwise, or cutting themselves with contaminated pieces of glass from breaking vessels.

During many medical procedures, one hand of a practitioner is used to hold a body portion or a vessel while the other hand inserts a needle, cuts with a scalpel, or performs other functions. Not infrequently, during such procedures, a practitioner can inadvertently stick himself with a needle or cut himself with a scalpel. Too, glass and other types of vessels containing blood and other body fluids sometimes break and a person holding the vessel ends up with cuts from fragments or slivers of broken glass or shards. These needle penetrations and cuts offer invasive paths for contaminants carried on the needles, scalpel blades and fragments or slivers.

Although it is increasingly important to protect such practitioners from possible contamination and consequent disease caused by viral and other agents within such invasive body fluids, gloves and vessel holding devices available at present provide insufficient protection in view of new and deadly viral and other contaminants now being encountered by various workers in medical, radiological, chemical and other fields.

SUMMARY OF THE INVENTION

In accordance with the present invention there is provided a protective hand forceps comprising a thumb encasing portion comprising an open unenclosed proximal end and a closed distal end, the distal end comprising a generally index finger-facing, gripping surface; an index finger encasing portion comprising an open unenclosed proximal end and a closed distal end, the distal end comprising a generally thumb-facing, gripping surface; structure for hinging together the proximal ends of the thumb and index finger encasing portions; and a skirt portion joining the thumb and index finger encasing portions for shielding the back of a user's hand. The gripping surfaces preferably comprise friction providing areas or structural grooves adapted to receive a predetermined device. The forceps of the invention can further comprise at least one shielding flange extending longitudinally along and laterally outward from the outside edge of at least one of the thumb and index finger encasing portions. Too, the distal ends of the thumb and index finger encasing portions can be formed into tool jaws. A center shield flange can be longitudinally disposed on and extend inwardly from either one of the thumb or index encasing portions. The skirt portion can comprise overlapping skirts extending from each of the thumb and index finger encasing portions. A soft latex-like coating can be provided to retain needles stabbing the forceps and to hold together the hard parts of the forceps if any part thereof shatters. The forceps can be constructed of plastic and can further comprise a spring steel strip disposed thereon to provide selected closure force resistance and the like. In the preferred embodiment, the closure force is preferably between about 50 and 250 dynes. The forceps can further comprise a ratchet structure for positioning the distal ends of the thumb encasing portion and the index finger encasing portion in a preselected fixed relationship to one another. The hinging means can comprise flexible plastic and can be of a smooth or a fluted structure. Tactile feedback ridges can be positioned within one or both of the thumb and index finger encasing portions to provide tactile response to a user. The tactile ridge preferably substantially follows the line of action of the forceps. Vents can be disposed on the encasing portions and can comprise, for example, overlapped spaced ridges, at least one of which can provide tactile stimulus to a user and between which structure can be disposed to inhibit entry of foreign physical structure into the forceps. Drainage canals or other drainage structure can be provided within the digit encasing portions to inhibit fluid accumulation therein.

It is therefore one object of the invention to protect a user's hand from inadvertent sharp implement penetration or cutting during various procedures.

Another object of the invention is to protect a user from cuts from shattering vessels held by the user.

Still another object of the invention is to provide good instrument, vessel and tool gripping capability.

One advantage of the invention is that in accordance therewith, mishandled needles are stoppable by a protective soft coating.

Another advantage of the invention is that modifications thereof can be used as tools themselves.

Other objects, advantages and novel features, and further scope of applicability of the present invention will be set forth in part in the detailed description to follow, taken in conjunction with the accompanying drawing, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention.

FIG. 1 illustrates a preferred embodiment of the invention;

FIG. 2 is a cutaway view of an embodiment of the invention having a fluted hinge and skirt area;

FIG. 3 shows an embodiment of the invention having a center shield;

FIGS. 4 and 5 depict embodiments of the invention having short straight and short angled tips;

FIG. 6 illustrates an alternative forceps embodiment of the invention settable in a fixed grip using complementary ratchet areas and cooperating center shield portions.

DETAILED DESCRIPTION OF THE INVENTION

Figure 9:
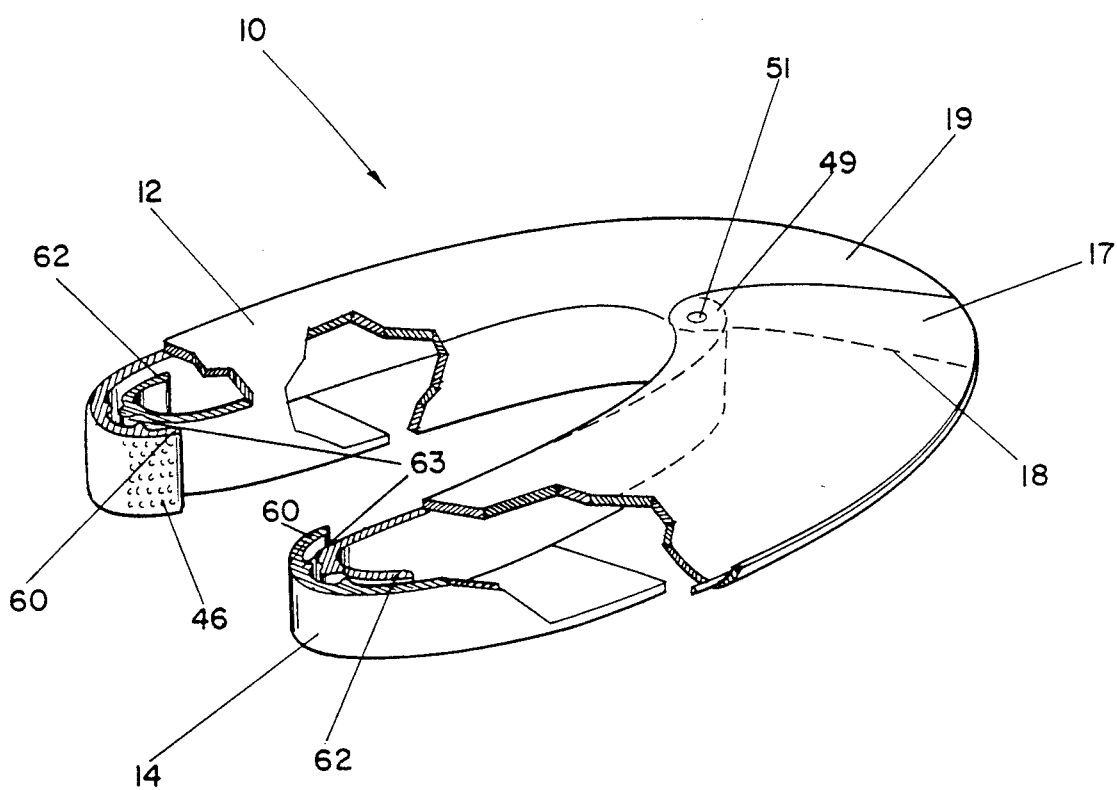
FIG. 9 is a showing of a hinged embodiment having overlapping skirt areas and vented distal tips in accordance with the present invention.

Reference is now made to FIG. 1 which shows a preferred embodiment of the invention. As seen therein, a protective hand forceps 10 comprises a thumb encasing portion 12, an index finger encasing portion 14, a hinging region 16 and a skirt area 18. The hinging region 16 and skirt area 18 are disposed at the proximal ends of the digit encasing portions. The distal ends of the thumb 12 and index finger 14 encasing portions 20 comprise gripping surfaces 20 and 22 facing one another. The forceps can comprise one shell sufficiently flexible in the hinging region 16 to provide for a desired amount of flexion or movement thereat. FIGS. 2 and 3 show an embodiment having fluted skirt areas 26 which provide suitable flexibility. Alternatively, as shown in FIG. 9, for example, the skirt area 18 can comprise overlapping skirts 17 and 19 extending back from the proximal ends of the thumb 12 and index finger 14 encasing portions. Hinge 49 of the FIG. 9 embodiment pivots on a pin 51. Those skilled in the art will recognize that forceps designed for various uses will differ in hinge construction and that the invention described herein is not limited to a particular hinge disclosed, there being many possible alternative ways of hinging a forceps in accordance with the invention, and that the hinges of the illustrated embodiments are only a few representations of many possible hinging structures for a hand forceps in accordance with the invention. The hinge can be used to provide a clamping or locking function, if desired, to retain an established grip between the distal gripping surfaces. The hinge can be designed to provide a preselected gripping force, if desired. A hinge which will open when sufficient spreading force is applied can also be used.

The forceps can be formed from plastic, metal or the like and can be molded entirely or in part. High density polyethylene, polystyrene and polyurethane can be used, for example. The forceps can be transparent, translucent or colored in particular ways, in whole or in part, in accordance with the needs for particular applications. The plastic used will in most cases be puncture proof in order to protect a wearer from inadvertently stabbing himself with a used hypodermic or IV needle. A forceps for surgical use will be scalpel proof. The forceps can be coated with an elastomer or latex-like material such as latex or silicone rubber to stop needles which penetrate the soft coating from deflecting off the forceps into a leg, wrist or other body part. Surgical forceps can be similarly coated to minimize trauma to body tissues gripped and otherwise contacted by the forceps. Such a coating will also hold together fragments of the forceps should it crush or break during a surgical procedure or otherwise. The plastic or other material used to fabricate the forceps should be sufficiently thick to afford the protection needed, but sufficiently thin to provide flexibility where necessary, such as in the hinging region. Certain embodiments of the forceps can comprise machined parts, such as tool forming distal tips. Too, a spring steel strip 28 (see FIGS. 1, 2, and 7-9) can be provided to bias the forceps to a preselected open position or to a closed position. Advantageously, steel is viewable by x-ray, and thus, the use of the spring steel strip 28 is particularly useful in forceps designed for use in surgery. The material from which it is constructed could be doped or coated with radioactive or stable isotope-containing, radio-opaque, or spin-labelled or otherwise NMR detectable chemical substances. The forceps can be used as hemostats or otherwise where corresponding metallic tools should not or could not be used. The forceps could comprise a fluorescent substance, or a fluorescent coating.

The particular shapes of the thumb 12 and index finger 14 encasing portions will vary with intended use. The distal ends can be rounded, blunt or flat, or they can be formed to perform a particular structural purpose. FIGS. 1, 7, 8, and 9 show generally flat, but somewhat rounded distal ends. FIGS. 4 and 5 show short straight and short angled distal ends or tips, respectively. Some forceps will be designed for use in handling IV needles, others for various surgical procedures and still others for handling test tubes and other vessels during laboratory analysis of body fluids, and the like. Different uses will dictate different distal end shapes as well as other modifications in accordance with the invention.

In the preferred embodiment, the dimensions of the forceps are such that a user's thumb and index finger will exert a force of about 50 to about 250 dynes to close the forceps. FIGS. 1, 2 and 7-9 show forceps having a spring steel strip 28 which provides additional stability to the forceps while allowing the forceps to be closed using a preselected amount of force.

Figure 7:
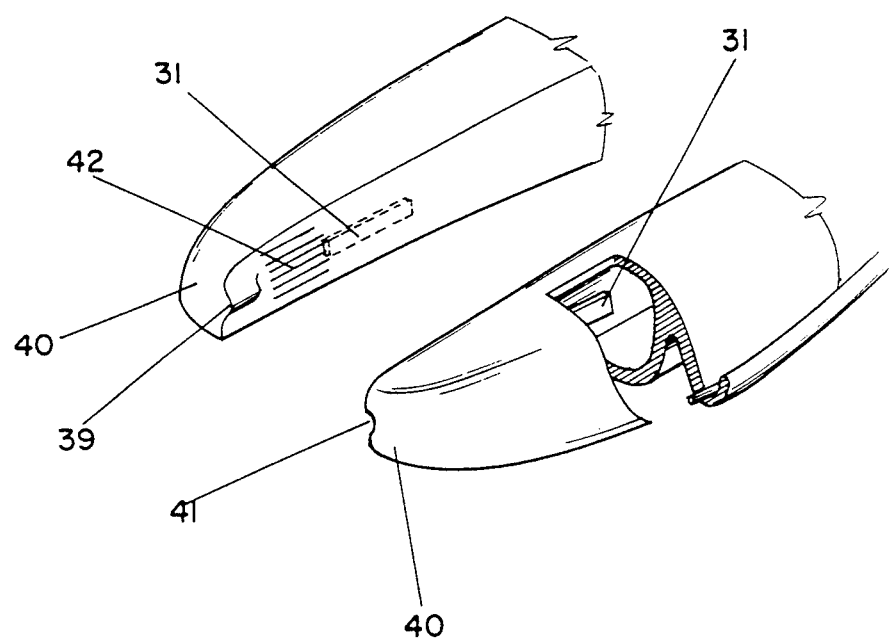
FIGS. 7 and 8 show smooth rat tooth tips and an alternative forceps holding distal tip.
Figure 8:
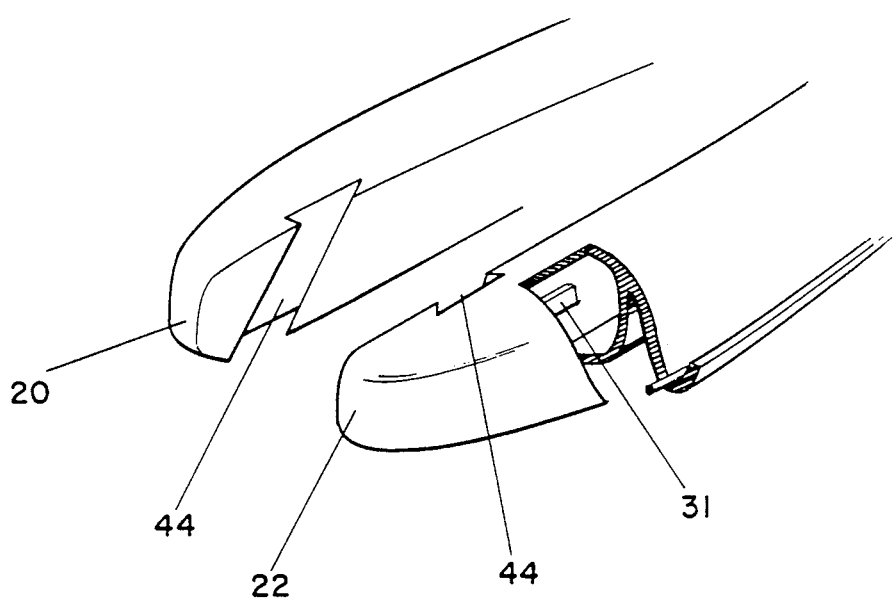

FIGS. 1, 4, 5, and 7-9 illustrate various representative distal tip configurations and gripping surfaces which can be utilized in the protective hand forceps of the invention. FIG. 1 shows gripping surfaces 20 and 22 which are relatively smooth, but which can comprise high to low friction surfaces. FIG. 4 shows somewhat extended straight distal tips 36 having fluted gripping surfaces 24 on tips 20 and 22. FIG. 5 shows somewhat extended angled distal tips 38 having cross-hatched gripping surfaces 25 on tips 20 and 22. FIG. 7 depicts a rat-tooth style distal tip arrangement 40 having several substantially parallel longitudinal ridges 42 and interlocking tongue 39 and groove 41. FIG. 8 shows locking distal tips, having forceps holding grooves 44. The FIG. 9 embodiment has dimpled surfaces 46 on the gripping surfaces. Cross hatching, raised indicia of sundry shape and etched lines, swirls and the like can also be used to enhance gripping surfaces 20 and 22. Distal tips can also be formed in various configurations to serve as tools.

The forceps can be vented, as shown in FIG. 9, to prevent fluid lock, thereby enabling easy hand removal. Overlapping ridges 60 and 62, preferably with knobs 63, prevent articles, such as curved suture needles, from slipping through vents and penetrating the hand of the user. Ridge 62 can also be somewhat pronounced to provide tactile indication to a user of hand placement and "feel". Although overlapping ridges 60 and 62 are shown facing toward one another in FIG. 9, on the facing surfaces, they could exit downward or outward to assure continuity in the gripping surfaces when desired. Although overlapping ridges 60 and 62 are shown positioned on the distal tips in FIG. 9, they could be positioned at any location on the forceps to provide venting.

FIG. 3 shows an embodiment of the invention incorporating a center shield 30 and outwardly laterally extending longitudinal flanges 32 and 34 on the digit encasing portions. The center shield 30 serves to stop needles and blades from penetrating between the encased finger and thumb of the wearer. The center shield 30 can extend toward and be biased toward the digit encasing portion to form a tight sliding relationship therewith so that no gap exists for a slipping needle or blade to enter. The outwardly laterally extending longitudinal flanges 32 and 34 act to stop needles, scalpel blades, and the like. The digit encasing portions 12 and 14 completely encase the digits in the distal ends of the forceps.

Tactile ridges 31, as shown in FIGS. 3 and 5-8 can be provided for a good "feel" or feedback from the forceps to the thumb and forefinger of a user. Preferably, tactile ridges 31 are disposed along the line of action of the tool. Tactile ridges 31 are particularly useful when the forceps is used in a location which cannot be easily seen to provide finger and tool location feedback to the user. Drainage grooves 47, as seen in FIG. 6, can be used to drain fluids which accumulate inside forceps. Ratchets 43 and 45, such as those illustrated in FIG. 6, can be used to provide forceps settable to selected gripping settings.

Fiber optics and/or electrodes can be incorporated into the forceps of the invention to provide a source of illumination, monitoring functions and to serve various other purposes which will be apparent to those skilled in the art.

Although the invention has been described with reference to these preferred embodiments, other embodiments can achieve the same results. Variations and modifications of the present invention will be obvious to those skilled in the art and it is intended to cover in the appended claims all such modifications and equivalents.

What is claimed is:

1. A substantially U-shaped protective hand forceps comprising:
   a thumb encasing portion comprising an open unenclosed proximal end and a closed distal end, said distal end comprising a generally index finger-facing, gripping surface:
   an index finger encasing portion comprising an open unenclosed proximal end and a closed distal end, said distal end comprising a generally thumb-facing, gripping surface;
   a discrete flexible hinge region for hinging together said proximal ends of said thumb and index finger encasing portions; and
   continuous skirt means joining said thumb encasing portion and said index finger encasing portion for providing continuous unopen shielding of the back of a user's hand to the thumb of the user's hand, said continuous skirt means extending only to the back of the user's hand and not to the palmar side of the user's hand.

2. The invention of claim 1 wherein said gripping surfaces comprises friction providing areas.

3. The invention of claim 1 wherein said gripping surfaces comprise grooves adapted to receive a predetermined device.

4. The invention of claim 1 further comprising at least one shielding flange extending longitudinally along and laterally outward from the outside edge of at least one of said thumb and index finger encasing portions.

5. The invention of claim 1 wherein said distal ends of said thumb and index finger encasing portions are formed into tool jaws.

6. The invention of claim 1 further comprising a center shield flange longitudinally disposed on and extending inwardly from at least one of said thumb and index encasing portions.

7. The invention of claim 1 wherein said forceps are constructed of plastic.

8. The invention of claim 7 wherein said plastic forceps comprise a spring steel strip.

9. The invention of claim 1 wherein said hinge region comprises flexible plastic.

10. The invention claim 1 wherein said hinge region comprises a fluted structure.

11. The invention of claim 1 further comprising at least one tactile feedback ridge positioned within at least one of said encasing portions for providing tactile response to a user.

12. The invention of claim 11 wherein said tactile ridge substantially follows the line of action of said forceps.

13. The invention of claim 1 wherein at least one of said encasing portions comprises means for venting.

14. The invention of claim 1 further comprising means for draining fluids which accumulate within said encasing portions.

15. The invention of claim 1 wherein said forceps closes under the exertion of between approximately 50 and 250 dynes closure force.

16. The invention of claim 1 wherein said forceps comprises a soft latex-like coating to retain sharp objects stabbing said forceps and to hold together said forceps if any part thereof shatters.

17. The invention of claim 1 wherein said forceps comprises at least one substance selected from the group consisting of radioactive isotopes, stable isotopes, radio-opaque chemical substances, spin-labelled substances, and fluorescent substances.

18. Protective hand forceps comprising:
    a thumb encasing portion comprising an open proximal end and a closed distal end, said distal end comprising a generally index finger-facing, gripping surface;
    an index finger encasing portion comprising an open proximal end and a closed distal end, said distal end comprising a generally thumb-facing, gripping surface;
    means for hinging together said proximal ends of said thumb and index finger encasing portions;
    skirt means joining said thumb encasing portion and said index finger encasing portion for shielding the back of a user's hand; and
    ratchet means for positioning said distal ends of said thumb encasing portion and said index finger encasing portion in a preselected fixed relationship to one another.

19. Protective hand forceps comprising:
    a thumb encasing portion comprising an open proximal end and a closed distal end, said distal end comprising a generally index finger-facing, gripping surface;
    an index finger encasing portion comprising an open proximal end and a closed distal end, said distal end comprising a generally thumb-facing, gripping surface;

means for hinging together said proximal ends of said thumb and index finger encasing portions;

skirt means joining said thumb encasing portion and said index finger encasing portion for shielding the back of a user's hand; and wherein at least one of said encasing portions comprises overlapping spaced ridges for venting.

20. The invention of claim 19 wherein at least one of said overlapping ridges is disposed to provide tactile stimulus to a user.

21. The invention of claim 19 further comprising means for inhibiting entry of a foreign physical structure into said forceps.

22. A substantially U-shaped protective hand forceps comprising:

a thumb encasing portion comprising an open unenclosed proximal end and a closed distal end, said distal end comprising a generally index finger-facing, gripping surface:

an index finger encasing portion comprising an open unenclosed proximal end and a closed distal end, said distal end comprising a generally thumb-facing, gripping surface;

pivot hinge means for hinging together said proximal ends of said thumb and index finger encasing portions; and overlapping skirts extending from each of said thumb and index finger encasing portions for providing continuous unopen shielding of the back of a user's hand to the thumb of the user's hand, said overlapping skirts extending only to the back of the user'-hand and not to the palmar side of the user's hand.

* * * * *